United States Patent
Schellekens et al.

(10) Patent No.: US 9,081,067 B2
(45) Date of Patent: Jul. 14, 2015

(54) PHASED ARRAY MR RF COIL WHICH IS NOT VISIBLE IN X-RAY IMAGE

(75) Inventors: Wayne Schellekens, Winnipeg (CA); Labros Petropoulos, Winnipeg (CA); Kirk Champagne, Winnipeg (CA); Mehran Fallah-Rad, Winnipeg (CA); Haoqin Zhu, Winnipeg (CA)

(73) Assignee: Imris Inc., Winnipeg, MB (CA)

( * ) Notice: Subject to any disclaimer, the term of this patent is extended or adjusted under 35 U.S.C. 154(b) by 586 days.

(21) Appl. No.: 13/455,849

(22) Filed: Apr. 25, 2012

(65) Prior Publication Data

US 2012/0286786 A1 Nov. 15, 2012

Related U.S. Application Data

(60) Provisional application No. 61/484,058, filed on May 9, 2011.

(51) Int. Cl.
*G01R 33/3415* (2006.01)
*A61B 6/04* (2006.01)
*G01R 33/36* (2006.01)
(Continued)

(52) U.S. Cl.
CPC .......... *G01R 33/3415* (2013.01); *A61B 6/0407* (2013.01); *A61B 6/4417* (2013.01); *A61B 5/0555* (2013.01); *A61B 6/5247* (2013.01); *A61N 2005/1055* (2013.01); *G01R 33/365* (2013.01); *G01R 33/4812* (2013.01)

(58) Field of Classification Search
CPC ............. G01R 33/365; G01R 33/3415; G01R 33/3685; G01R 33/3642

USPC .................................................. 324/300–322
See application file for complete search history.

(56) References Cited

U.S. PATENT DOCUMENTS 5,491,415 A  2/1996 Holmes
5,666,055 A  9/1997 Jones
(Continued)

FOREIGN PATENT DOCUMENTS

WO  WO 2009146521  12/2009
WO  WO 2009146522  12/2009
(Continued)

OTHER PUBLICATIONS

Monroe J W et al: "Phased Array Coils for Upper Extremity MRA", Magnetic Resonance in Medicine, Academic Press, Duluth, MB, US, vol. 33, No. 2, Feb. 1, 1995, pp. 224-229, XP000482946, ISSN: 0740-3194 *Chapter "Coil Design"*.

(Continued)

*Primary Examiner* — Dixomara Vargas
(74) *Attorney, Agent, or Firm* — Adrian D. Battison; Ade & Company Inc.

(57) ABSTRACT

An phased array RF coil used for MR imaging is designed so that it remains in place in the field of view of an X-Ray imaging system and comprises a support board on which copper or aluminum conductive traces are carried. The attenuation of the X-Rays caused by the traces is visible in the radiation image but this is compensated by arranging the non-conductive material of the support board such that the attenuation is substantially constant. The phased array includes individual coil loops which are overlapped with the traces being of half thickness at crossing locations of the traces and with one of the loops on one side and the other loop on the second side of the substrate sheet.

20 Claims, 6 Drawing Sheets

(51) Int. Cl.
 *G01R 33/48* (2006.01)
 *A61B 6/00* (2006.01)
 *A61N 5/10* (2006.01)
 *A61B 5/055* (2006.01)

(56) References Cited

U.S. PATENT DOCUMENTS

| | | | |
|---|---|---|---|
| 6,300,761 B1 * | 10/2001 | Hagen et al. | 324/318 |
| 6,900,637 B1 * | 5/2005 | Seeber | 324/318 |
| 6,925,319 B2 | 8/2005 | McKinnon | |
| 7,282,915 B2 * | 10/2007 | Giaquinto et al. | 324/318 |
| 7,382,132 B1 * | 6/2008 | Mathew et al. | 324/318 |
| 7,394,251 B2 * | 7/2008 | Lin | 324/309 |
| 7,394,254 B2 | 7/2008 | Rieke | |
| 7,570,054 B1 * | 8/2009 | Lin | 324/309 |
| 7,619,413 B2 * | 11/2009 | Wiggins et al. | 324/318 |
| 7,683,620 B2 * | 3/2010 | Lin | 324/309 |
| 7,728,592 B2 * | 6/2010 | Ma et al. | 324/318 |
| 7,804,300 B2 * | 9/2010 | Possanzini | 324/318 |
| 8,487,615 B2 * | 7/2013 | Zhu et al. | 324/307 |
| 8,723,522 B2 * | 5/2014 | Ma et al. | 324/318 |
| 8,797,029 B2 * | 8/2014 | Zhu et al. | 324/307 |
| 8,866,481 B2 * | 10/2014 | Zhu et al. | 324/318 |
| 2008/0129296 A1 | 6/2008 | Fischer | |

FOREIGN PATENT DOCUMENTS

| | | |
|---|---|---|
| WO | WO 2011000085 | 1/2011 |
| WO | WO 2011022896 | 3/2011 |

OTHER PUBLICATIONS

Rieke V et al: "X-ray Compatible Radio frequency Coil for Magnetic Resonance Imaging", Magnetic Resonance in Medicine Wiley USA, vol. 53, No. 6, Jun. 2005, pp. 1409-1414, XP002682215, ISSN: 0740-3194.

* cited by examiner

PHASED ARRAY MR RF COIL WHICH IS NOT VISIBLE IN X-RAY IMAGE

This application claims the benefit under 35 USC 119(e) of Provisional Application 61/484,058 filed May 9, 2011.

This invention relates to a phased array RF coil formed of a series of separate coil elements or individual loops for use in magnetic resonance imaging which can be used to obtain MR images of a body part of a patient and can remain in place during X-Ray imaging of the body part without interfering with the X-Ray image. The coil array can be used for receive functions, transmit functions or can carry out both functions.

BACKGROUND OF THE INVENTION

Magnetic resonance imaging (MRI) is commonly employed for medical imaging. In addition, combined use of MRI with radiation (X-Ray) therapy and with radiation imaging have both been used in a number of prior situations. Such systems provide significant advantages compared to single modality systems for obtaining information of the patient. However in such prior dual imaging systems, the patient may need to be moved or transferred from one system to another system. Such transfers can be difficult and time-consuming, and they can compromise results by complicating image registration.

MRI in combination with a radiotherapy accelerator has been used. Thus the X-Rays must be transmitted through the RF coil of the MR imaging system which remains in place during the radiotherapy. Although the RF coils of the MRI system are in the radiation path, they do not cause enough absorption to significantly degrade therapy or require a higher dose for imaging. For example the RF coils may have an equivalent Al thickness of about 2.3 mm, which is sufficiently low for the therapy to be carried out without interference from the coil and low enough not to affect the optimal dose of X-Ray radiation.

The combination of MRI with radiation imaging or more specifically X-Ray imaging causes unique problems. Specifically, if a conventional surface MRI Receive Coil is placed in the imaging path of a X-Ray system, the coil will be visible in the image and will cause artifacts or edges or components of the receive coil may cover important features in the X-Ray image which are required to be seen by the surgeon. For this reason, when MRI is performed in combination with radiation imaging, all coils of the MRI system, including the RF coils, are typically disposed out of or removed from the radiation path so as to be outside the field of view.

For example, U.S. Pat. No. 6,925,319 (McKinnon) issued Aug. 2, 2005 considers a split magnet MRI system having all MRI coils disposed out of the radiation path of an X-Ray system.

Unfortunately, MRI performance can be undesirably degraded by a requirement to place the MRI RF coils outside the field of view of a radiation imaging system. For example, surface RF coils are often placed directly on a subject being imaged for maximum MRI image quality. Such a surface coil is in the field of view of any radiation imaging system that is directed to the same part of the subject as the MRI system. Thus conventional combined MRI and radiation imaging can require an undesirable choice among accepting reduced MRI image quality by placing the RF coils out of the radiation system field of view, accepting RF coil artifacts in the radiation images by placing the RF coils in the radiation system field of view, or by moving the MRI RF coils to one position for MRI imaging and to another position out of the field of view for radiation imaging.

U.S. Pat. No. 7,394,254 (Rieke) issued Jul. 1, 2008 discloses using aluminum for the RF coils to render them "transparent" to X-Ray. More particularly, the patent discloses an arrangement in which improved compatibility of MRI with radiation imaging is provided by MRI RF coils having transmissive coil sections. The transmissive coil sections are substantially transparent to the penetrating radiation employed by the radiation imaging system. Thus the transmissive coil sections can be disposed in a field of view of the radiation imaging system without introducing artifacts into the radiation images. Transparency to penetrating radiation can be achieved by substantially including only low atomic number (i.e., $Z<29$) elements in the transmissive coil sections. Preferably, the transmissive coil sections are fabricated substantially from aluminum.

However it is accepted that the use of aluminum for the traces of an RF coil leads to a degradation in the MR imaging relative to the use of copper. However copper cannot be used in a trace which is sufficiently thin to generate the "transmissive" coil sections of Rieke.

Related disclosures are made in published PCT Applications WO 2009/146521 and 2009/146522 both filed May 25, 2009 and published Dec. 10, 2009 by the present Applicants/Assignees, the disclosures of which are incorporated herein by reference or to which reference may be made for further detail.

In PCT Application WO 2011/000085 filed Jun. 29, 2010 and published 6 Jan. 2011 by the present Applicants/Assignees is disclosed an RF coil where the conductive traces of the RF coil are arranged of a conductive material which has a thickness such that the traces cause an attenuation of the penetrating electromagnetic radiation which is visible in the radiation image and the support board includes non-conductive material in the field of view which has a thickness selected such that an attenuation of the penetrating electromagnetic radiation at locations on the board spaced from the traces is substantially equal to the attenuation at locations on the board at the conductive traces. However this arrangement does not disclose how to provide a phased array coil of this type where the attenuation is constant which has individual loops which, as is previously known, must overlap for decoupling mutual inductance between the coil loops. The disclosures of this document are incorporated herein by reference or to which reference may be made for further detail.

In PCT Application WO 2011/022896 published 3 Mar. 2011 by the present assignees is disclosed an RF coil loop including arrangements for decoupling and pre-amplification. The disclosures of this document are incorporated herein by reference or to which reference may be made for further detail.

SUMMARY OF THE INVENTION

It is one object of the present invention to provide an phased array RF coil suitable for use in a dual imaging system using MRI and penetrating radiation such as X-Rays.

According to a first aspect of the invention there is provided an RF phased array coil for use in an MR imaging system for generating an MR image of the subject and in a radiation imaging system for generating a radiation image of a subject using penetrating electromagnetic radiation the phased array coil being arranged to remain in place during the radiation imaging and including coil conductive traces located in the field of view of the radiation imaging;

the RF phased array coil comprising:

a support defined by at least one substrate sheet;

a plurality of individual coil loops formed by conductive traces carried on the substrate;

at least one of the individual coil loops being overlapped with at least one other of the individual coil loops so that a leg of said one coil loop lies adjacent to a leg of said other coil loop with two sections at ends of the leg of said one coil loop crossing two corresponding sections at ends of the leg of said other coil loop;

each of the crossing sections and each of the corresponding sections has a thickness in a direction at right angles to the substrate which is less than that of the legs.

Preferably each of the crossing sections and each of the corresponding sections has a thickness in a direction at right angles to the substrate which is equal to one half of that of the legs.

Preferably each of the individual coil loops has a thickness along the full length thereof, with the exception of crossing sections and corresponding sections, which is constant.

Preferably said one of said individual coil loops is arranged on a first surface of the substrate sheet and said other of the individual coil loops is arranged on a second opposed surface of the substrate sheet.

Preferably the support comprises first and second overlying laminated substrate sheets and wherein said one of said individual coil loops is arranged on a first surface of the first substrate sheet and said other of the individual coil loops is arranged on a second opposed surface of the first substrate sheet so as to be located between the first and second substrate sheets.

Preferably there is provided a third of the individual coil loops which is located on a second opposed surface of the second substrate sheet and wherein the third individual coil loop is overlapped with said one and said other of the individual coil loops.

Preferably the conductive traces of the RF coil are arranged of a conductive material which has a thickness such that the traces cause an attenuation of the penetrating electromagnetic radiation which is visible in the radiation image and wherein the support substrate includes non-conductive material in the field of view which has a thickness selected such that an attenuation of the penetrating electromagnetic radiation at locations on the substrate sheet spaced from the traces is substantially equal to the attenuation at locations on the substrate sheet at the conductive traces.

Preferably the non-conductive material of the support substrate sheet is arranged relative to the conductive traces such that the attenuation of the penetrating electromagnetic radiation of substantially the whole of the RF coil located within the field of view is substantially constant throughout the field of view.

In one arrangement the support substrate sheet is formed from common material and wherein the thickness of the common material is varied so that the attenuation of the penetrating electromagnetic radiation of substantially the whole of the RF coil located within the field of view is substantially constant throughout the field of view.

In another arrangement the support substrate sheet is formed from a base material and an additional material different from the base material is added to the support substrate sheet so that the attenuation of the penetrating electromagnetic radiation of substantially the whole of the RF coil located within the field of view is substantially constant throughout the field of view, where the base material and the additional material are preferably laminated to form a common structure.

Preferably the support substrate sheet is flexible.

Preferably the conductive traces are formed of copper.

The conductive traces are preferably formed of aluminum to reduce the attenuation but the same concepts can be used where the conductive traces are formed of copper.

Preferably the support substrate sheet is formed of fiber reinforced resin such as FR-4.

According to a second aspect of the invention there is provided an RF phased array coil for use in an MR imaging system for generating an MR image of the subject and in a radiation imaging system for generating a radiation image of a subject using penetrating electromagnetic radiation the phased array coil being arranged to remain in place during the radiation imaging and including coil conductive traces located in the field of view of the radiation imaging;

the RF phased array coil comprising:

a support defined by at least one substrate sheet;

a plurality of individual coil loops formed by conductive traces carried on the substrate;

at least one of the individual coil loops being overlapped with at least one other of the individual coil loops so that a leg of said one coil loop lies adjacent to a leg of said other coil loop with two sections at ends of the leg of said one coil loop crossing two corresponding sections at ends of the leg of said other coil loop;

wherein said one of said individual coil loops is arranged on a first surface of the substrate sheet and said other of the individual coil loops is arranged on a second opposed surface of the substrate sheet.

While taking X-ray images, if a coil is present then the components and conductive traces are visible in the X-Ray Image. For a MR phased coil array, the conductive elements or loops must be overlapped to provide decoupling of adjacent elements. Where the traces overlap, the x-ray sees a double thickness, and thus raises the total aluminum equivalence that we would have to match. This is true for any conductive material whether that be aluminum where the attenuation is low or copper where it is much higher.

Various materials give different attenuation based on their thickness. Copper traces on a MR coil element appear as grey bars in an X-Ray image. A similar attenuation can be given by plastic or other non-conductive material based on its thickness.

Where conduction coil element traces overlap, the trace is reduced in thickness to approximately one-half the metal thickness giving a uniform x-ray aluminum equivalence across the region. The technique can be applied to any material with an atomic number less than 30.

This can easily be achieved in standard printed circuit manufacturing starting with a board that has one-half the metal thickness, applying a mask layer resist over the conductor overlap region, and electroplating the board to form the traces to the desired thickness.

The coils traces are also interleaved from the front and the back of the substrate to maintain the same X-ray aluminum equivalency.

Preferably the non-conductive material of the support board is arranged relative to the conductive traces such that the attenuation of the penetrating electromagnetic radiation of substantially the whole of the RF coil located within the field of view is substantially constant throughout the field of view. There may however be points or areas where the attenuation is different and an alternative system is used to remove these points or areas from the image. It will be appreciated that such attenuation is not invisible in the image but is instead visible in the sense that it is sufficient to affect the image so that its presence can be determined. However the intention is that the attenuation is constant or homogeneous so that there is no visible artefact within the image and the presence of the RF coil within the image does not affect the changes of image intensity at the various locations within the image which are caused by the differences in attenuation caused by the part being imaged.

In one arrangement, preferably the support board is formed from common material and wherein the thickness of the common material is varied so that the attenuation of the penetrating electromagnetic radiation of substantially the whole of the RF coil located within the field of view is substantially constant throughout the field of view.

In another arrangement, the support board is formed from a base material and an additional material different from the base material is added to the support board.

In both cases the material can be machined to provide the required thicknesses as determined by analyzing the difference in attenuation caused by the materials themselves relative to the copper traces and calculating the required thickness.

Materials can be selected for the additional material or for the board itself which have a very high attenuation so that the thickness of the material is not significantly different from the copper traces.

Conventional techniques and materials for manufacturing the support board can be used including printing the traces or etching the traces as required. Thus the term "traces" is not intended to limit the conductors to any particular method of formation of the conductors on the support board.

Preferably the base material and the additional material are laminated to form a common structure.

Preferably the conductive traces are continuous throughout the field of view so as to have a constant thickness and therefore attenuation. Many techniques are available for forming such continuous traces with out the necessity for joints which may double the thickness at certain locations or may require connecting material such as solder. Thus preferably the conductive traces include no solder within the field of view.

Preferably there are no connector wires from the conductive traces within the field of view so that the connector wires such as coaxial connectors, wires and rods which connect from the traces to the pre-amplifier or other location are located outside the field of view.

In many cases it is necessary to locate the tuning capacitors required for such a coil to be located within the field of view and preferably it is arranged such that the capacitor has an attenuation of the penetrating electromagnetic radiation which is substantially equal to the attenuation of the conductive traces.

This can be achieved where the capacitor is formed from conductive traces with a dielectric material between the traces to define the required capacitance.

In many cases it is also necessary to locate a fuse required for such a coil to be located within the field of view and preferably it is arranged such that the attenuation of the penetrating electromagnetic radiation by the fuse is substantially equal to the attenuation of the conductive traces.

This can also be achieved where the fuse is formed from conductive traces.

Preferably the support board includes no mechanical mounting and support structures within the field of view.

The support board may be flexible.

In many cases it is also necessary to provide a diode for the RF coil and where possible this can be located outside the field of view.

In some cases it is necessary to locate within the field of view a diode or other similar element which has an attenuation different from the conductive traces. In this case the location of the diode in the field of view is arranged to be constant and the image of the diode or other element in the radiation image is removed by software image analysis.

Preferably the conductive traces are formed of copper but other similarly conductive materials can be used instead of aluminum which is effectively transparent to the X-Rays but is generally unsuitable for RF coil manufacture.

The support board can be formed of any suitable nonconductive material which is MR compatible and has an attenuation to X-Rays which is less than or around that of copper such as FR-4 fibreglass circuit board.

BRIEF DESCRIPTION OF THE DRAWINGS

The following FIGS. 1 to 5 are taken from the above mentioned PCT application WO 2011/000085 published 6 Jan. 2011.

DETAILED DESCRIPTION

The following description is taken from the above PCT application and is included for completeness of disclosure herein.

Figure 1:
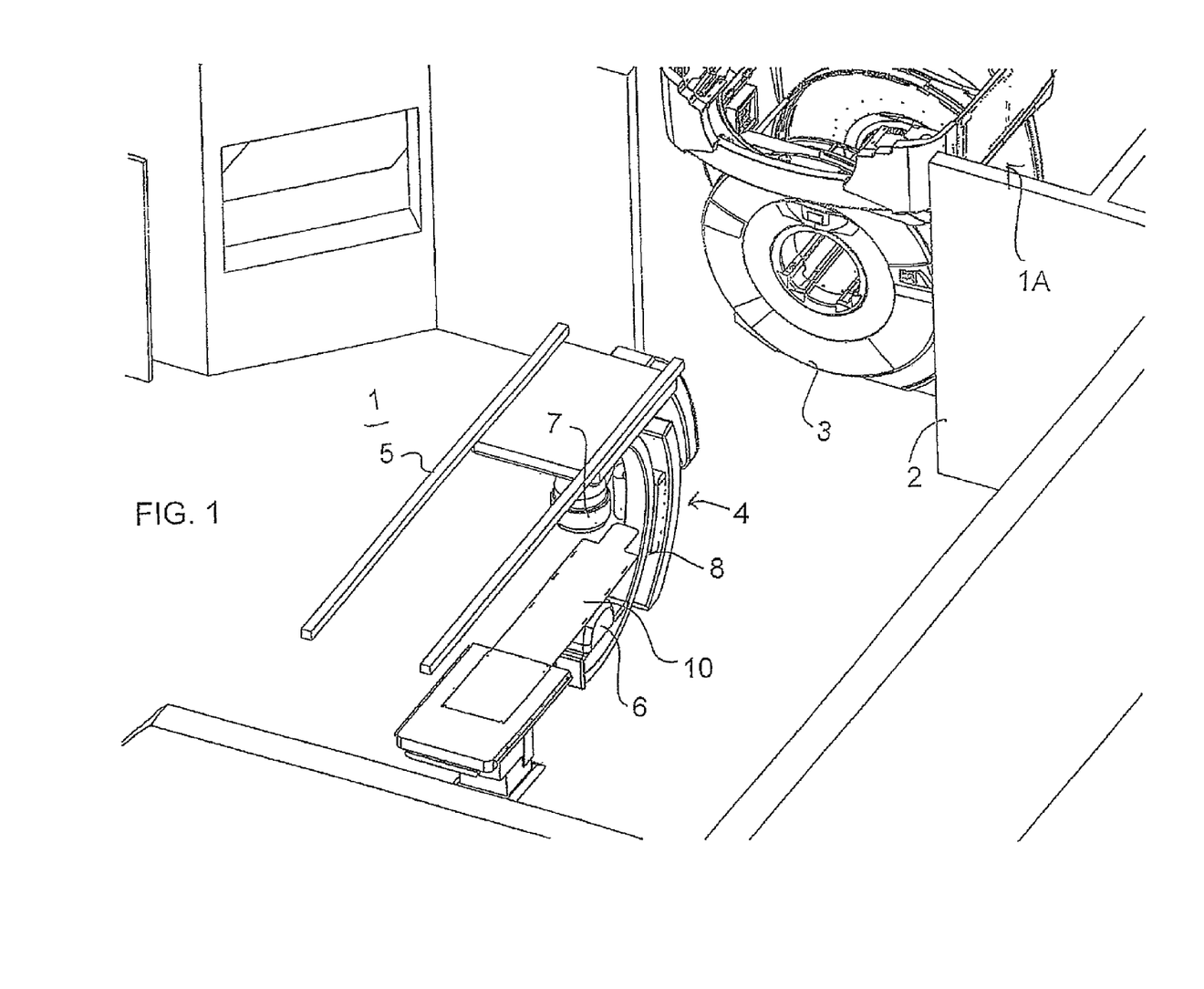
FIG. 1 is an isometric view of an Angiography room showing a patient table, an MRI magnet movable into a position for imaging the patient on the table and an arrangement for moving an X-Ray system.

In FIG. 1 is shown an arrangement for carrying out Magnetic Resonance Imaging and X-Ray imaging of a patient while the patient remains stationary on a patient support table. The arrangement provides a room 1 in which is mounted a patient support table 10 with doors 2 at one side of the room for entry into the room of the magnet 3 of an MR imaging system from a magnet bay 1A. The room contains an X-Ray imaging system 4 mounted on rails 5 and includes an X-Ray transmitter 6 and receiver 7 mounted on a C-shaped support 8. The X-Ray system is of a conventional construction commercially available from a manufacturer such as Siemens. The table 10 described and illustrated herein is used in an arrangement where the patient remains in position on the table while imaging is effected using MRI and X-Ray.

The X-Ray system 4 which co-operates with the moving magnet described above such that the patient can be imaged by either modality on the same table. The patient does not move and at least one of the RF coils remains in place.

The MR is a high-field (e.g. 1.5 T or 3 T or more) magnet that moves on overhead rails between the two or more rooms as described above. In the system described, one or more of these rooms contains an X-Ray system, either a single-plane or a biplane. When the magnet is moved out of the X-Ray examination room and a set of RF and X-Ray shielded doors is closed, the examination room functions as a conventional X-Ray lab and can be used with conventional equipment. In particular, X-Ray guided interventions may be performed.

The arrangement may be used in a typical three room configuration with the Angiography Room (AR) on the left, a Diagnostic Room (DR) in the middle, and an Operating Room on the right. The magnet moves on overhead rails between the rooms and can image in each.

When MR imaging is required, the X-Ray equipment is safely stowed, the doors open, and the magnet is brought into the room over the patient on the table. The RF shield encompasses the AR so all the equipment in the X-Ray examination room is made RF-quiet. MR imaging can then be performed. Afterwards, the magnet is removed from the room, the doors closed, and the X-Ray equipment is returned to its working position.

The MR scanner is used to provide information complementary to that obtained using X-Ray. It can be used, for example, to perform a baseline assessment prior to intervention as well as to perform a post-intervention assessment. Such an assessment may include perfusion and viability studies of, for example, the heart or of the brain.

In the arrangement for moving the X-Ray system as shown in FIG. 1 the MR enters the X-Ray examination room and moves over the head end of the table 10. Since the path of the MR passes right through the location of the C-arm stands, the latter must be moved before the magnet may enter. Depending on need, a floor-mounted C-arm stand may be moved on floor rails, floor turntable, or a boom mounted on the floor or wall. Depending on need, a ceiling-mounted C-arm stand may be moved using extended rails to park it at the foot end of the table, by mounting the stand rails on a platform suspended from the movable magnet rails, or by fixing the stand rails on a platform with a telescopic arm to move them laterally.

Using a solution to move a floor-mounted stand together with a mover for a ceiling mounted stand provides a mechanism to move a biplane system. The mover can provide a mounting position of the single plane or biplane at some non-zero angle to the MR rails, e.g., 90 degrees.

Figure 2:
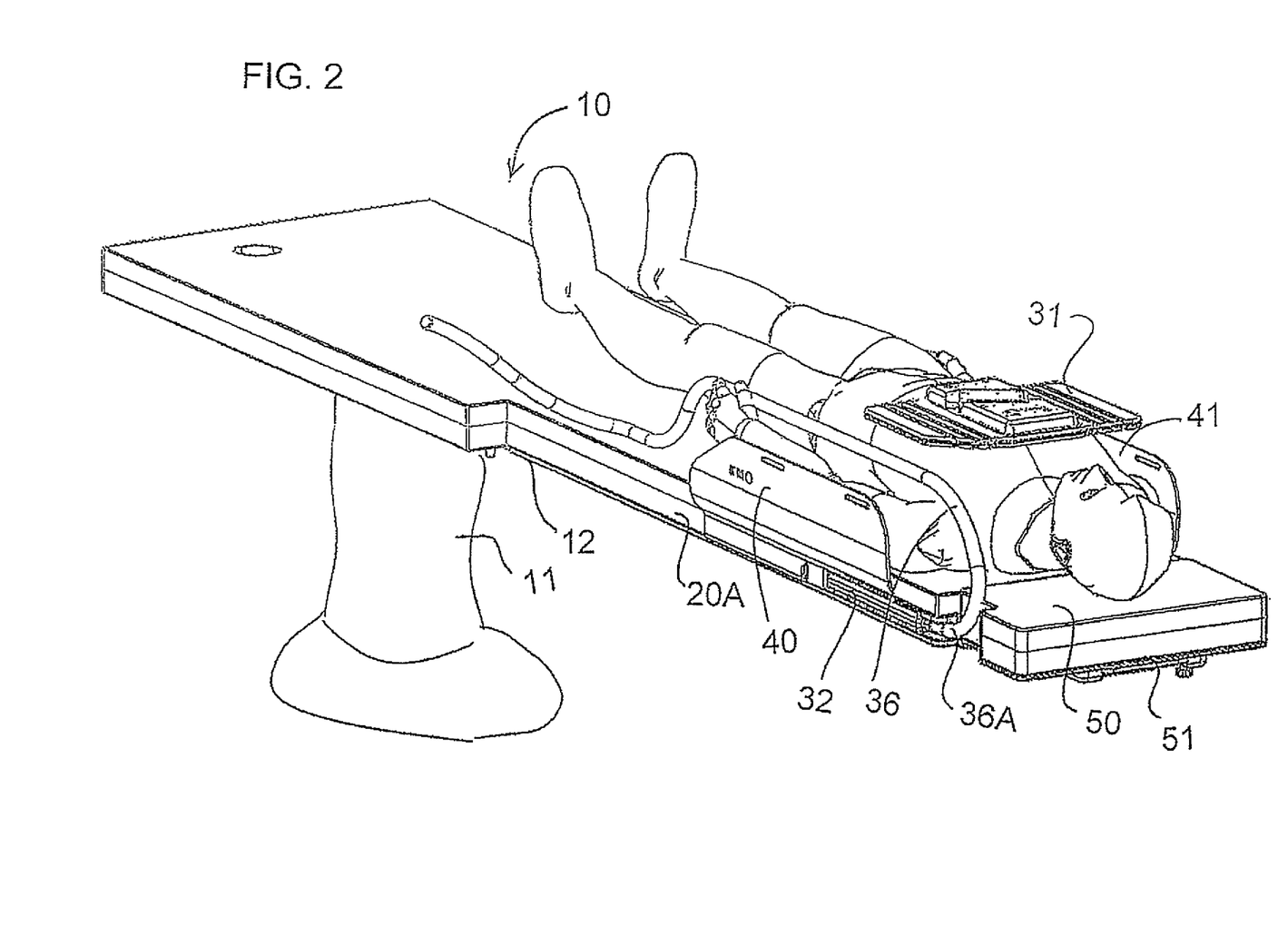
FIG. 2 is an isometric view of a table for mounting the patient, the base being omitted for convenience of illustration, and showing the RF coil construction for imaging of the upper torso of the patient.

The Patient Handling System or support table is shown in FIG. 2 as indicated generally at 10. The patient support table includes a base 11 of a conventional construction which allows the base to move a patient support portion 12 to required locations in height and in orientation. Suitable drive mechanisms and couplings are known in the art and thus are not required to be described herein. At the top of the base 11 is mounted the patient support portion in the form of a generally planar body 12 formed of a fiber reinforced plastics material so as to define a surface area sufficient for supporting the patient while lying on the patient support portion.

When the imaging is to be of the chest, an anterior chest coil 31 is arranged to be placed on top of the chest of the patient when in place for imaging on the mattress and also the posterior coil 32 is arranged to be place behind the patient. Similarly when imaging is to be of the head, coils are placed above and below the head of the patient.

In order to avoid moving the patient when changing from the MR imaging system to the X-Ray imaging system, at least the posterior coil remains in place. Thus this coil will be visible in the X-Ray image. The imaging system may be a simple linear X-Ray system or more preferably is a bi-planar rotating system of the type illustrated which takes multiple images around the patient.

Thus the apparatus for use in imaging of a part of a patient as shown in FIG. 1 includes the radiation imaging system 4 for generating a radiation image of a subject in the field of view using penetrating electromagnetic radiation and the magnetic resonance imaging system for generating an image of the subject including the magnet 3 and the RF coils 31, 32.

Figure 3:
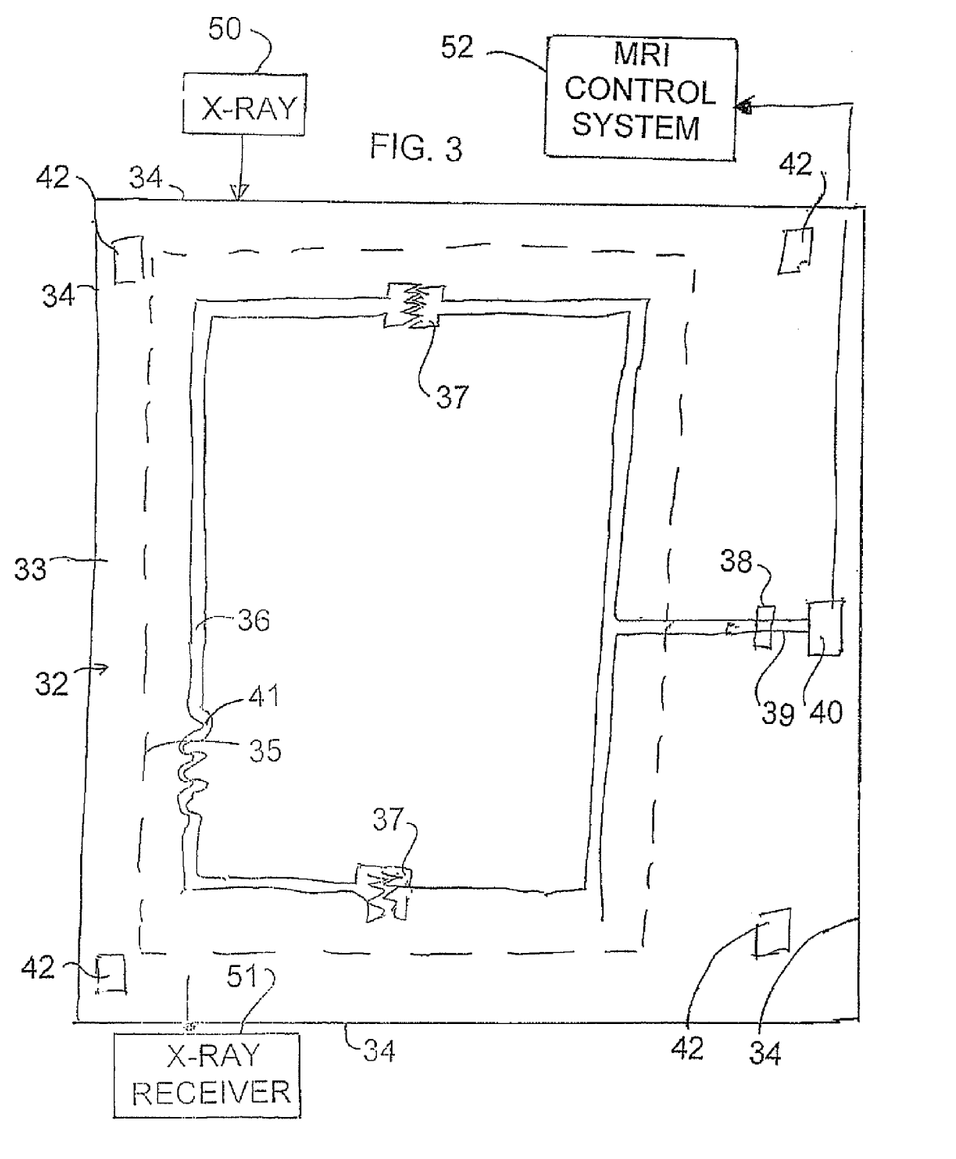
FIG. 3 is a plan view of the RF coil including the components of the system attached thereto which are shown schematically.
Figure 4:
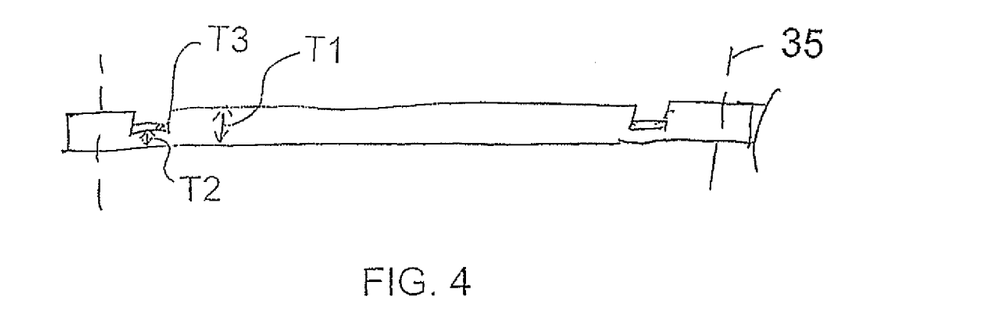
FIG. 4 is a cross sectional view through the RF coil.

A schematic illustration of the RE coil 32 is shown in FIGS. 3 and 4 and is arranged to remain in place during the radiation imaging using the X-Ray transmitter 50 and receiver 51 shown only schematically.

The RF coil includes a support board 33 having side edges 34 and the imaging system 4 defines a field of view 35 within the area of the board which can be seen in the X-Ray image with portions of the board outside the field of view being outside the image.

The circuitry of the coil includes conductive traces 36, capacitors 37, a fuse 41, a diode 38, a connecting wire 39, and a pre-amplifier 40. All of these elements are conventional in general construction and are well known to persons skilled in the art of coil design so that detailed explanation is not required here.

The conductive traces of the RE coil are arranged of a conductive material and typically copper which has a thickness T3 of at least 0.0007 inch and preferably in the range 0.0014 inch to 0.0042 inch which is effective to receive the RF signals from the MR imaging system. Such traces typically cause an attenuation of the penetrating electromagnetic radiation which is clearly visible in the radiation image as compared with a uniform thickness support board material.

As shown in FIG. 4, the support board is formed of a non-conductive material in the field of view which has a thickness T1 at locations on the board spaced from the traces selected such that an attenuation of the penetrating electromagnetic radiation at those locations is substantially equal to the attenuation at the conductive traces. Thus the attenuation of the board material at thickness T1 is arranged so that it is equal to the sum of the attenuation caused by the thickness T3 of the trace and thickness T2 of the board at the trace. In this way the attenuation of the penetrating electromagnetic radiation of substantially the whole of the RF coil located within the field of view is substantially constant throughout the field of view.

While the traces are shown in FIG. 4 recessed into shallow areas of the board, the traces can be applied on top of the flat board and the variable thickness of the board applied at the rear. In addition, the board may be flat by filling recesses with a material which is transparent to X-Ray and thus does not affect the attenuation.

Figure 5:
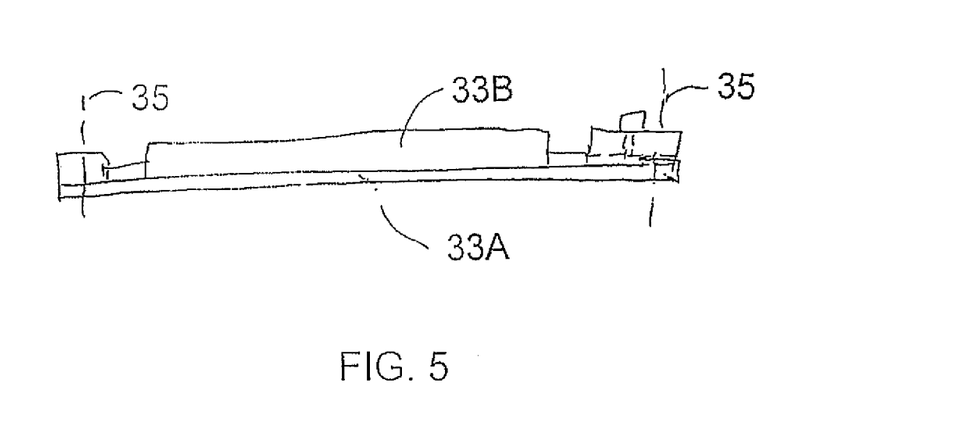
FIG. 5 is a cross sectional view through the RF coil showing a modified construction.

In FIG. 5 is shown an alternative arrangement in which the board is formed of a base material 33A and an additional material 33B is added to the support board at areas separate from the traces, which material is non-conductive and has an attenuation factor that is it is not transparent to X-Ray and is different from the base material 33A. The base material and the additional material are laminated to form a common structure and the recesses may be filled by additional transparent material.

The conductive traces are arranged to be continuous throughout the field of view so as to have a constant attenuation. That is the conductive traces include no joints and therefore no solder within the field of view. Instead the traces are printed or otherwise applied as a constant continuous strip. Alternatively the traces are formed by etching away unwanted material from a continuous layer on the board leaving traces which are continuous and without joints.

As shown in FIG. 3 all connector wires 39 from the coil are located outside the filed of view 35 there are no connector wires from the conductive traces within the field of view.

The capacitors 37 and the fuse 41 for the coil are in most cases necessarily located within the field of view 35 and these are therefore arranged so that the attenuation of the penetrating electromagnetic radiation is substantially equal to the attenuation of the board at the conductive traces. Thus the capacitor and the fuse is itself formed from conductive traces which are designed and laid out on the board with the required amount of conductive material and the dielectric material to provide the required characteristics and values. The design of such components from conductive traces is known and within the skill of a person skilled in this art.

The support board includes mechanical mounting and support structures 42 for connection of the board to necessary elements but these are designed and arranged so that they are outside the field of view so that the board is generally constant and continuous and there are no mechanical structures within the field of view.

The necessary diode 38 is designed and arranged on the traces so that it is located outside field of view.

As an alternative, the diode or other necessary element is located within the field of view where the element has an attenuation different from the conductive traces and of a construction and high attenuation factor such that it cannot reasonably be compensated for by building the remainder of the board up to this high attenuation factor. In this arrangement, where element is located in the field of view, the location of the element in the field of view is constant and the image of the element in the radiation image is removed by software image analysis at the X-Ray receiver system 51.

Figure 6:
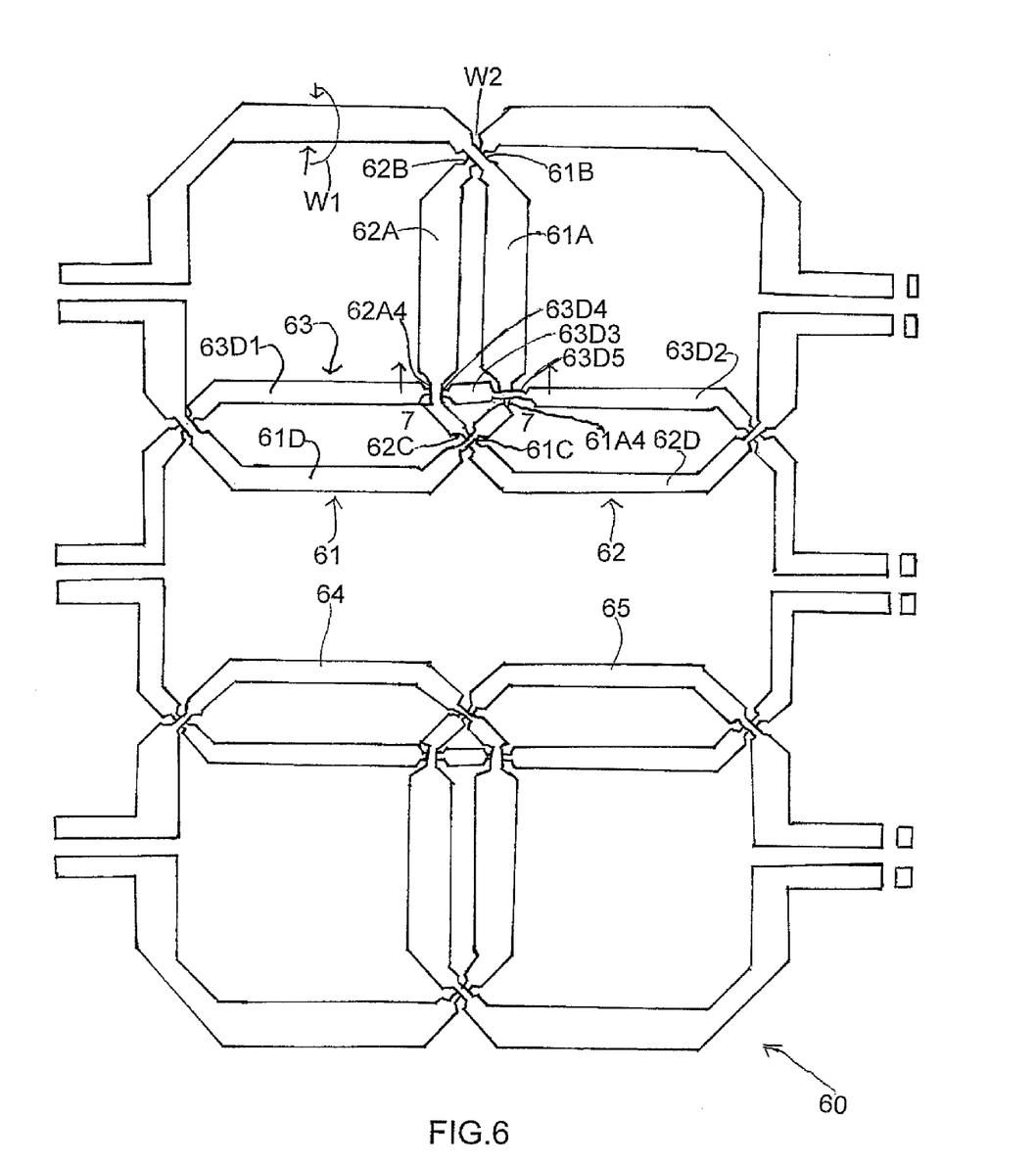
FIG. 6 is a plan view of a phased array coil according to the present invention.
Figure 7:
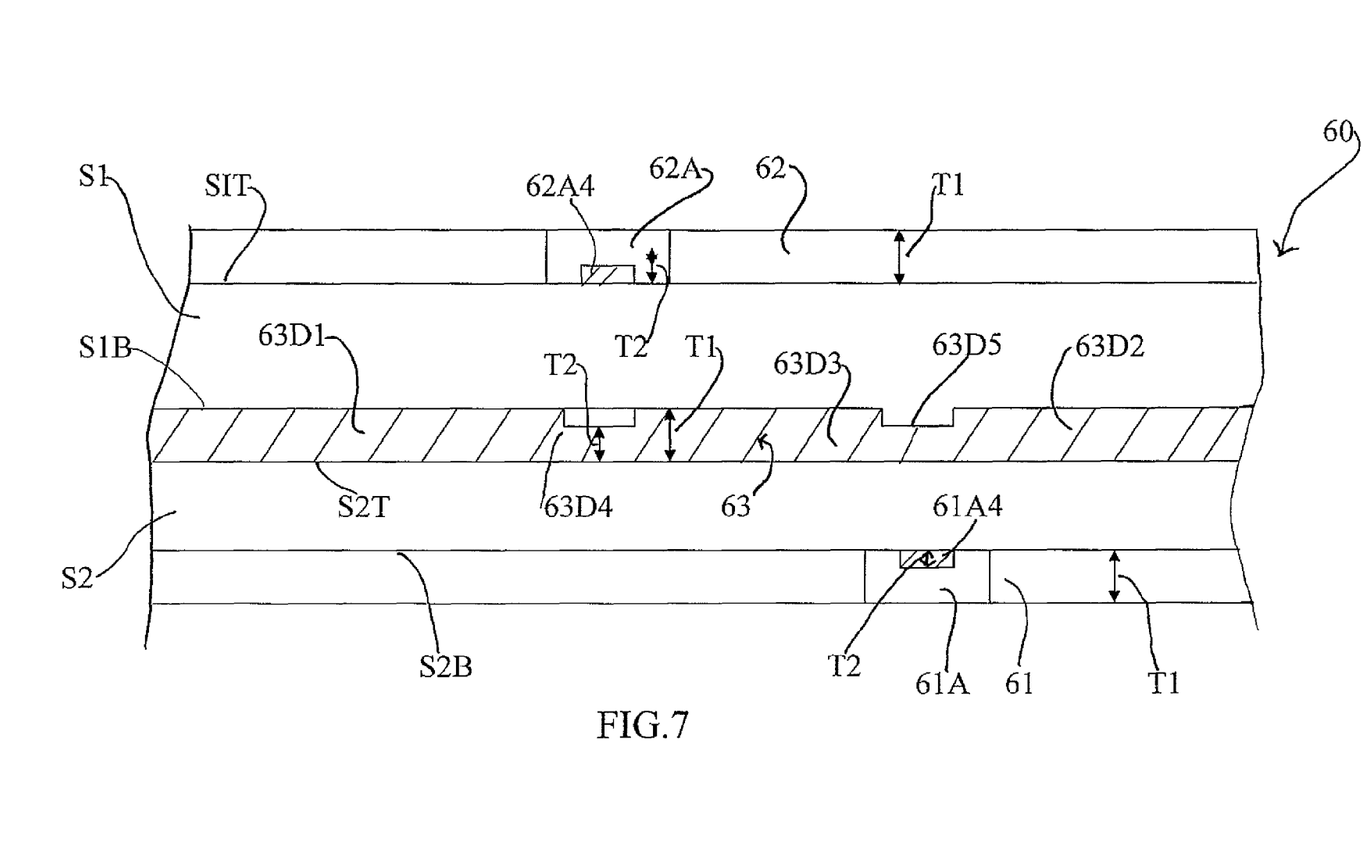
FIG. 7 is a cross-sectional view along the lines 7-7 of FIG. 6.

Turning now to FIGS. 6 and 7 there is shown a modification according to the present invention, where the remaining parts of the coil not mentioned are as disclosed above.

The RF phased array coil shown in FIG. 6 includes a support 60 defined by a single substrate sheet or as shown in FIG. 7 two substrate sheets S1 and S2.

On the substrate 60 is mounted a plurality of individual coil loops 61 to 65 formed by conductive traces carried on the substrate.

The individual coil loops 61 and 62 are overlapped with each other so that a leg 62A of loop 62 lies adjacent to a leg 61A of loop 61 with two sections 62B and 62C at ends of the leg 62A of loop 62 crossing two corresponding sections 61B and 61C at ends of the leg 61A of coil loop 61.

At each crossing such as crossings 61B, 62B, the width of the trace is reduced from a width W1 at the remainder of the trace to a width W2 at the crossing. This is a known technique to reduce capacitive coupling between the loops for purposes of assisting in de-coupling the loops.

A review of the pattern shown in FIG. 6 will show that loop 63 overlaps in symmetrical manner loops 61 and 62 to form leg 63D1 which lies alongside leg 61D and leg 63D2 which lies alongside leg 62D. Each leg has crossing points at its ends. The legs 63D1 and 63D2 cross leg 62A at crossing 63D4 and leg 61A at crossing 63D5 forming a short section 63D3 between the crossings. The crossing section 63D4 crosses a corresponding section 62A4 of the leg 61. Also a symmetrical arrangement is made between coils 63, 64 and 65.

This general lay out of loops for phased array coils is previously known but the present invention provides a manner in which the individual loops can be decoupled using the known overlapping layout and also can be invisible in an X-ray image.

As shown in FIG. 7, of the crossing sections 63D4 and 63D5 and each of the corresponding sections 62A4 and 61A4 has a thickness T2 in a direction at right angles to the substrate S1, S2 which is less than the thickness T1 of the legs 63D1, 63D2, 63D3, 62A and 61A.

Typically each of the crossing sections and each of the corresponding sections has the thickness T2 equal to one half of thickness T1 and each of the individual coil loops 61, 62 and 63 has the constant thickness T1 along the full length thereof, with the exception of crossing sections and corresponding sections.

As shown in FIG. 6, individual coil loop 62 is arranged or printed on the first or top (in the orientation shown) surface S1T of the substrate sheet S1 and the individual coil loop 63 is arranged on a second opposed surface S1B of the substrate sheet S1. In an arrangement wherein only loops 62 and 63 are provided with no additional overlapping loop 61, the substrate is formed by only the single sheet S1. However in the arrangement shown with the loop 61 included and overlapping with both, the second sheet S2 is provided on the bottom of the loop 63 so that its top surface S2T engages the loop 63 with the loop 62 on the bottom surface S2B of the sheet S2.

Thus the conductive traces 61, 62 and 63 of the RF coil arranged of a conductive material have a thickness such that the traces cause an attenuation of the penetrating electromagnetic radiation which is visible in the radiation image and, as explained above in relation to the cited prior application, the support substrate includes non-conductive material in the field of view which has a thickness selected such that an attenuation of the penetrating electromagnetic radiation at locations on the substrate sheet spaced from the traces is substantially equal to the attenuation at locations on the substrate sheet at the conductive traces. It will be noted that the overlapping sections are arranged with the thickness T2 over a length which matches almost so that the summation of the thickness of the loops measured over the whole coil surface is T!. Thus this can be matched with a thickness of the substrate or a material applied to the substrate to provide a constant aluminum equivalent value over the whole coil structure within the intended field of view of the X-ray system.

As explained previously, the support substrate sheet can formed of single material of different thicknesses. Alternatively the support can be formed from a base material and an additional material different from the base material is added to the support substrate sheet so that the attenuation of the penetrating electromagnetic radiation of substantially the whole of the RF coil located within the field of view is substantially constant throughout the field of view.

The support formed by substrate sheets S1 and S2 is preferably flexible but this is not essential.

The conductive traces can be formed of copper or aluminum or other suitable materials well known to a person skilled in this art.

The support substrate sheets S1 and S2 are formed of fiber reinforced resin such as FR-4.

The invention claimed is:

1. An RF phased array coil for use in an MR imaging system for generating an MR image of the subject and in a radiation imaging system for generating a radiation image of a subject using penetrating electromagnetic radiation, the phased array coil being arranged to remain in place during the radiation imaging and including coil conductive traces located in the field of view of the radiation imaging;

the RF phased array coil comprising:
a support comprising a substrate sheet having opposed first and second surfaces;
a plurality of individual coil loops formed by conductive traces carried on the substrate sheet on at least one of said top and bottom surfaces;
at least one of the individual coil loops being overlapped with at least one other of the individual coil loops so that a leg of said one coil loop lies adjacent to a leg of said other coil loop with two sections at ends of the leg of said one coil loop crossing two corresponding sections at ends of the leg of said other coil loop;

each of the crossing sections and each of the corresponding sections has a thickness in a direction at right angles to the top and bottom surfaces of the substrate sheet which is less than that of the legs.

2. The apparatus according to claim 1 wherein each of the crossing sections and each of the corresponding sections has a thickness in a direction at right angles to the substrate sheet which is equal to one half of that of the legs.

3. The apparatus according to claim 1 wherein each of the individual coil loops has a thickness along the full length thereof, with the exception of crossing sections and corresponding sections, which is constant.

4. The apparatus according to claim 1 wherein said one of said individual coil loops is arranged on the first surface of the substrate sheet and said other of the individual coil loops is arranged on the second opposed surface of the substrate sheet.

5. The apparatus according to claim 1 wherein the support comprises an additional substrate sheet laminated to said second opposed surface of said substrate sheet such that said other of the individual coil loops is located between said substrate sheet and said additional substrate sheet.

6. The apparatus according to claim 5 wherein there is provided a third of the individual coil loops which is located on a surface of said additional substrate sheet opposite to said substrate sheet and wherein the third individual coil loop is overlapped with said one and said other of the individual coil loops.

7. The apparatus according to claim 1 wherein the conductive traces of the RF coil are arranged of a conductive material which has a thickness such that the traces cause an attenuation of the penetrating electromagnetic radiation which is visible in the radiation image and wherein the support substrate includes non-conductive material in the field of view which has a thickness selected such that an attenuation of the penetrating electromagnetic radiation at locations on the substrate sheet spaced from the traces is substantially equal to the attenuation at locations on the substrate sheet at the conductive traces.

8. The apparatus according to claim 7 wherein the non-conductive material of the support substrate sheet is arranged relative to the conductive traces such that the attenuation of the penetrating electromagnetic radiation of substantially the whole of the RF coil located within the field of view is substantially constant throughout the field of view.

9. The apparatus according to claim 8 wherein the support substrate sheet is formed from common material and wherein the thickness of the common material is varied so that the attenuation of the penetrating electromagnetic radiation of substantially the whole of the RE coil located within the field of view is substantially constant throughout the field of view.

10. The apparatus according to claim 8 wherein the support substrate sheet is formed from a base material and an additional material different from the base material is added to the support substrate sheet so that the attenuation of the penetrating electromagnetic radiation of substantially the whole of the RF coil located within the field of view is substantially constant throughout the field of view.

11. The apparatus according to claim 10 wherein the base material and the additional material are laminated to form a common structure.

12. The apparatus according to claim 1 wherein the support substrate sheet is flexible.

13. The apparatus according to claim 1 wherein the conductive traces are formed of copper.

14. The apparatus according to claim 1 wherein the conductive traces are formed of aluminum.

15. The apparatus according to claim 1 wherein the support substrate sheet is formed of fiber reinforced resin.

16. The apparatus according to claim 1 wherein the support substrate sheet is formed of FR-4.

17. An RF phased array coil for use in an MR imaging system for generating an MR image of the subject and in a radiation imaging system for generating a radiation image of a subject using penetrating electromagnetic radiation the phased array coil being arranged to remain in place during the radiation imaging and including coil conductive traces located in the field of view of the radiation imaging;

the RF phased array coil comprising:

a support comprising a substrate sheet having opposed first and second surfaces;

a plurality of individual coil loops formed by conductive traces carried on the substrate sheet;

at least one of the individual coil loops being overlapped with at least one other of the individual coil loops so that a leg of said one coil loop lies adjacent to a leg of said other coil loop with two sections at ends of the leg of said one coil loop crossing two corresponding sections at ends of the leg of said other coil loop;

wherein said one of said individual coil loops is arranged on a first surface of the substrate sheet and said other of the individual coil loops is arranged on a second opposed surface of the same substrate sheet with said substrate sheet forming a single substrate sheet between said individual coil loops and said other of the individual coil loops.

18. The apparatus according to claim 17 wherein the support comprises an additional substrate sheet laminated to said second opposed surface of said substrate sheet such that said other of the individual coil loops is located between said substrate sheet and said additional substrate sheet, wherein there is provided a third of the individual coil loops which is located on a second opposed surface of the second substrate sheet and wherein the third individual coil loop is overlapped with said one and said other of the individual coil loops.

19. The apparatus according to claim 17 wherein the conductive traces of the RF coil are arranged of a conductive material which has a thickness such that the traces cause an attenuation of the penetrating electromagnetic radiation which is visible in the radiation image and wherein the support substrate includes non-conductive material in the field of view which has a thickness selected such that an attenuation of the penetrating electromagnetic radiation at locations on the substrate sheet spaced from the traces is substantially equal to the attenuation at locations on the substrate sheet at the conductive traces.

20. The apparatus according to claim 17 wherein the non-conductive material of the support substrate sheet is arranged relative to the conductive traces such that the attenuation of the penetrating electromagnetic radiation of substantially the whole of the RF coil located within the field of view is substantially constant throughout the field of view.

* * * * *